United States Patent [19]
Whalen et al.

[11] Patent Number: 5,562,598
[45] Date of Patent: Oct. 8, 1996

[54] ARTIFICIAL URETHRAL SPHINCTER

[75] Inventors: Robert L. Whalen, Cambridge, Mass.; Michael J. Sarrasin, Nashua, N.H.

[73] Assignee: Whalen Biomedical Inc., Somerville, Mass.

[21] Appl. No.: 309,144

[22] Filed: Sep. 20, 1994

[51] Int. Cl.$^6$ ........................................................ A61F 2/02
[52] U.S. Cl. ...................................... 600/29; 128/DIG. 25
[58] Field of Search ................ 600/29–32; 128/DIG. 25

[56] References Cited

U.S. PATENT DOCUMENTS

| | | | |
|---|---|---|---|
| 4,222,377 | 9/1980 | Burton | 128/DIG. 25 |
| 4,571,749 | 2/1986 | Fischell | 128/DIG. 25 |
| 4,634,443 | 1/1987 | Haber | 600/31 |
| 4,850,963 | 7/1989 | Sparks et al. | 128/DIG. 25 |

FOREIGN PATENT DOCUMENTS 526357  9/1976  U.S.S.R. ........................ 128/DIG. 25

*Primary Examiner*—Angela D. Sykes
*Assistant Examiner*—John P. Lacyk

[57] ABSTRACT

A magnetically operated artificial urethral sphincter for the treatment of total urinary incontinence is presented. The artificial urethral sphincter employs an external magnet to achieve closure of the urethral cuff, a hydraulically operated silicone rubber sphincter cuff. The proposed invention consists of the urethral cuff, a connecting tube, and an elastomeric bellows assembly. The invention is closed by an external magnet placed on the skin over the implanted reservoir assembly. When the external magnet is in place the elastomeric bellows of the reservoir is compressed, and the prosthetic sphincter is closed. Removal of the external magnet from the skin over the implant allows the bellows to expand, thus opening the urethral cuff.

8 Claims, 3 Drawing Sheets

ARTIFICIAL URETHRAL SPHINCTER

LICENSE RIGHTS

The U.S. government has a paid up license in this invention and the right, in limited circumstances to require the patent owner to license others on reasonable terms as provided by the terms of SBIR Phase II Grant DK42752 awarded by the National Institute of Health.

BACKGROUND-FIELD OF INVENTION

This invention relates to artificial urethral sphincters, as are used to mitigate the effects of urinary incontinence.

BACKGROUND-DESCRIPTION OF PRIOR ART

The National Institutes on Aging has estimated that more than 12 million Americans are incontinent. It is the second most common reason for institutionalization of the elderly, generating costs at nearly eight billion dollars a year. An artificial urethral sphincter thus has wide potential applicability in this large and growing patient population. Urinary incontinence that is treatable with an artificial urethral sphincter includes a spectrum of medical conditions common in this patient group, such as surgical injury following transurethral resection or radical prostatectomy, neurologic injury, or direct injury to the sphincter itself.

The present invention pertains generally to the treatment of urinary incontinence and more particularly to an incontinent bladder control method and apparatus incorporating a prosthesis for selectively restricting urine flow in a urethra.

Both males and females have an external sphincter formed about the urethra which, when functioning normally, constricts the urethra and prevents flow of urine from the bladder except when the bladder is voided during normal urination.

There are numerous prior art prosthetic sphincters for selectively closing and opening the urethra to prevent incontinence. These devices typically incorporate an inflatable cuff which surrounds the urethra or encloses it on two sides, and which is inflated to restrict urine flow in the urethra. Examples of such prosthetic sphincters are seen in Fischell U.S. Pat. No. 4,571,749, and Burton U.S. Pat. No. 4,222,377.

The artificial sphincter developed by Burton, U.S. Pat. No. 4,222,377 consists of three silicone rubber components and connecting tubing. There is an inflatable urethral cuff, a balloon reservoir/pressure source, and a pump. The cuff is implanted around the bladder neck in women, and around the bulbous urethra in most males. The implanted cuff functions similarly to a blood pressure cuff. When the cuff is filled with pressurized fluid, it occludes the urethra and stops the flow of urine. The cuff pressure is regulated by a pressure regulating balloon. The balloon is inflated with a specified volume of fluid and the tension in the balloon wall maintains a predetermined pressure, usually in the range of 60 cm of $H_2O$.

In order to adjust the cuff pressure with this design, the balloon must be exchanged, requiring a surgical procedure. The pump assembly, implanted in the scrotum in males and the labia in females, is connected between the cuff and balloon.

Normally, the cuff and balloon are at the same equilibrium pressure, occluding the urethra. When the patient wishes to urinate, he or she squeezes the pump, temporarily transferring fluid from the cuff to the balloon. The urethra opens, and the patient's bladder empties.

The pump assembly then slowly bleeds fluid back to the cuff from the balloon, causing the cuff to inflate over a period of approximately five minutes. Thus, the proper function of the Burton prosthesis depends upon the action of the pump and the check valve system, miniature implantable components subject to mechanical failure. The use of this prosthesis is also somewhat constraining to the patient, as its action is not instantaneous, particularly during reinflation of the cuff.

A major drawback to device in this configuration is that if it should fail through loss of working fluid, it will remain in the closed position resulting in a medical emergency.

Other known artificial sphincter control devices inject a fluid into the cuff to compress the urinary passage or remove fluid from it to release the passage and allow urination. These devices can be implanted in the patients abdomen, and operated through the skin.

In the absence of any hardware device passing through the skin, currently the only simple manipulation which can performed through the skin is to exert pressure on an implanted control device, by pressing with a finger. Also the continence state is the usual state, with the result that the artificial sphincter must remain pressurized for long periods, being released only during urination, a disadvantage similar to the device above.

There is already known from U.S. Pat. No. 4,571,749 an implantable urinary sphincter system in which the control device comprises a bellows connected to a vessel filled with incompressible fluid comprising a flexible membrane. When the patient presses hard with the fingers on the membrane the length of the bellows is increased which in turn increases the volume of a chamber filled with incompressible liquid connected to the sphincter, so reducing the pressure in the sphincter. On the other hand when no pressure is exerted on the membrane, the return force exerted by a diaphragm constituting one wall of the chamber tends to return the latter to its original volume, so as to compress the sphincter.

This device has a number of disadvantages, however. Firstly, the action of the patient on the membrane may not result in sufficient lengthening of the bellows because of the shape of the membrane or because the vessel may expand rather than the bellows. What is more, the end of the surface of the bellows is small, which does not guarantee effective action of the bellows on the chamber.

An objective of the present invention is to avoid these disadvantages. The present invention is reliable safe and readily usable by patients with limited dexterity. The present invention employs an external magnet to achieve closure of the prosthetic sphincter, a hydraulically operated silicone rubber urethral cuff. The invention consists of the sphincter cuff, connecting tube, and an elastomeric bellows reservoir assembly. The sphincter is closed by an external magnet placed on the skin over the implanted reservoir assembly. When the external magnet is in place, the elastomeric bellows of the reservoir is compressed, and the prosthetic sphincter is closed. Removal of the external magnet from the skin over the implant allows the bellows to expand, thus opening the sphincter.

The external magnet is retained in place by magnetic attraction to a second magnet located within the implanted reservoir. It is thus worn by the patient on the skin over the reservoir. To deflate the urethral cuff the patient simply removes the external magnet. Upon completion of micturation, the external magnet is returned to its proximate position over the implant.

Other advantages of this magnetically actuated sphincter includes a simple percutaneous adjustment of urethral cuff pressure, and a default mode which cannot injure the patient in the event device function is lost, it will revert back to an open condition if the external magnet is lost or if the working fluid leaks from the system.

SUMMARY OF THE INVENTION

It is an object of the present invention to provide a method and apparatus for treatment of incontinent bladder function which overcomes the above enumerated disadvantages which are inherent in prior art devices.

It is another object of the invention to provide a prosthesis which is simply constructed, and which may be easily used by a patient with limited dexterity.

It is yet another object of the invention to provide a prosthesis which is implanted in the body and actuated by the application or removal of an external magnet on the external skin over the site of the implanted device.

It is yet another object of the invention to employ an internal magnet constructed of highly efficient magnetic material, such as neodymium-iron boron, to provide the forces of actuation.

It is yet another object of the invention to provide an external magnet constructed of highly efficient magnetic material, such as neodymium-iron boron, to provide the forces of actuation.

It is still another object of the invention to provide a prosthesis which provides for the increase or decrease of working fluid, in the elastomeric bellows, through a percutaneous access port.

It is still another object of the present invention to provide a textured jacket over an implantable reservoir to minimize tissue capsule formation around the implanted reservoir.

It is yet another object of the present invention to provide a prosthesis which has an inflatable cuff, capable of being inflated through the collapse of the elastomeric bellows, which when inflated radially and inwardly compresses the urethra, thus holding back urine.

Further objects, features and advantages obtained by the instant invention will become apparent when the following detailed description of a preferred embodiment is in view of the accompanying drawings.

DESCRIPTION OF THE DRAWINGS

The structure, operation, and advantage of this invention will become further apparent upon consideration of the following description taken in conjunction with the accompanying drawings wherein.

DETAILED DESCRIPTION OF THE INVENTION

Figure 1:
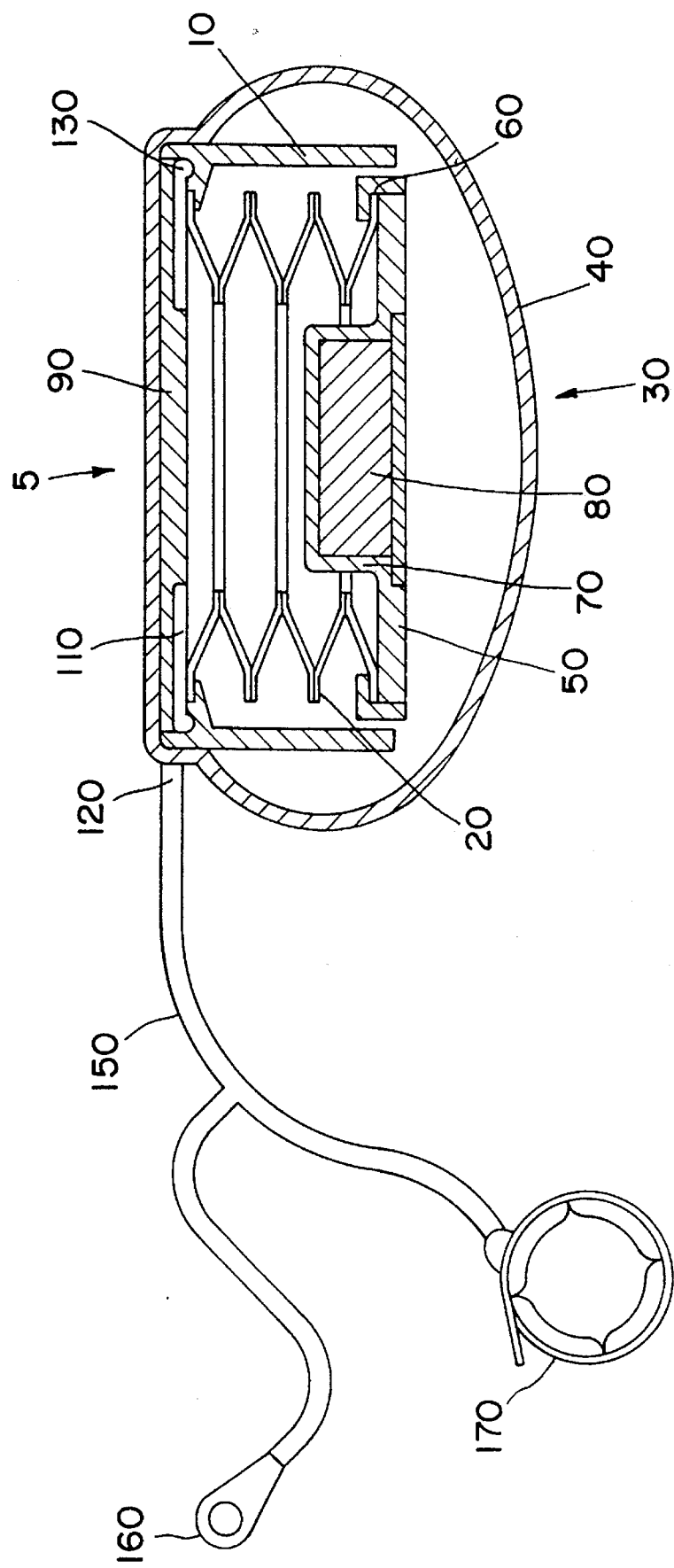
FIG. 1 is a partially sectioned assembly view of the artificial urethral sphincter.

Turning now to the drawings, and more particularly to FIG. 1, an artificial urethral sphincter 5 is presented. A pump reservoir housing 10 is shown. Surrounding pump reservoir housing 10 is elastomeric jacket 30, constructed of a biocompatible material, such as silicone. Elastomeric jacket 30 incorporates a textured exterior surface 40. Elastomeric jacket 30 performs several functions, it prevents cellular infiltration, and lessens fibrous tissue formation by virtue of textured surface 40.

Encased in pump reservoir housing .10 is elastomeric bellows 20. Elastomeric bellows 20 is attached to lower reservoir cover 50 via a clamp ring 60. Extending out from the center portion of lower reservoir cover 50 and into elastomeric bellows 20 is magnet well 70. Inside magnet well 70 is magnet 80.

Terminal end of elastomeric bellows 20 is attached to upper reservoir cover 90 via bellows retention joint 100. Engraved on the obverse side, and bored into upper reservoir cover 90, are fluid channels 110. Fluid channels 110 allow fluid to move, when elastomeric bellows 20 is collapsed or open, into fluid port 120. Fluid port 120 is beveled into upper reservoir cover 90 allowing for fluid channels 120 to channel fluid into and out of elastomeric bellows 20 via fluid plenum 130.

Attached to end of fluid port 120 is fluid conduit 150, comprised of a biocompatible material utilizing textured surface 40. Fluid conduit 150 is bifurcated with one bifurcation leading to fluid infusion port 160. Fluid infusion port 160 allows the fluid level inside elastomeric bellows 20 to be adjusted percutaneously. The second bifurcation of fluid conduit 150 leads to urethral cuff 170. Urethral cuff 170 fits over and around a urethra.

Figure 2:
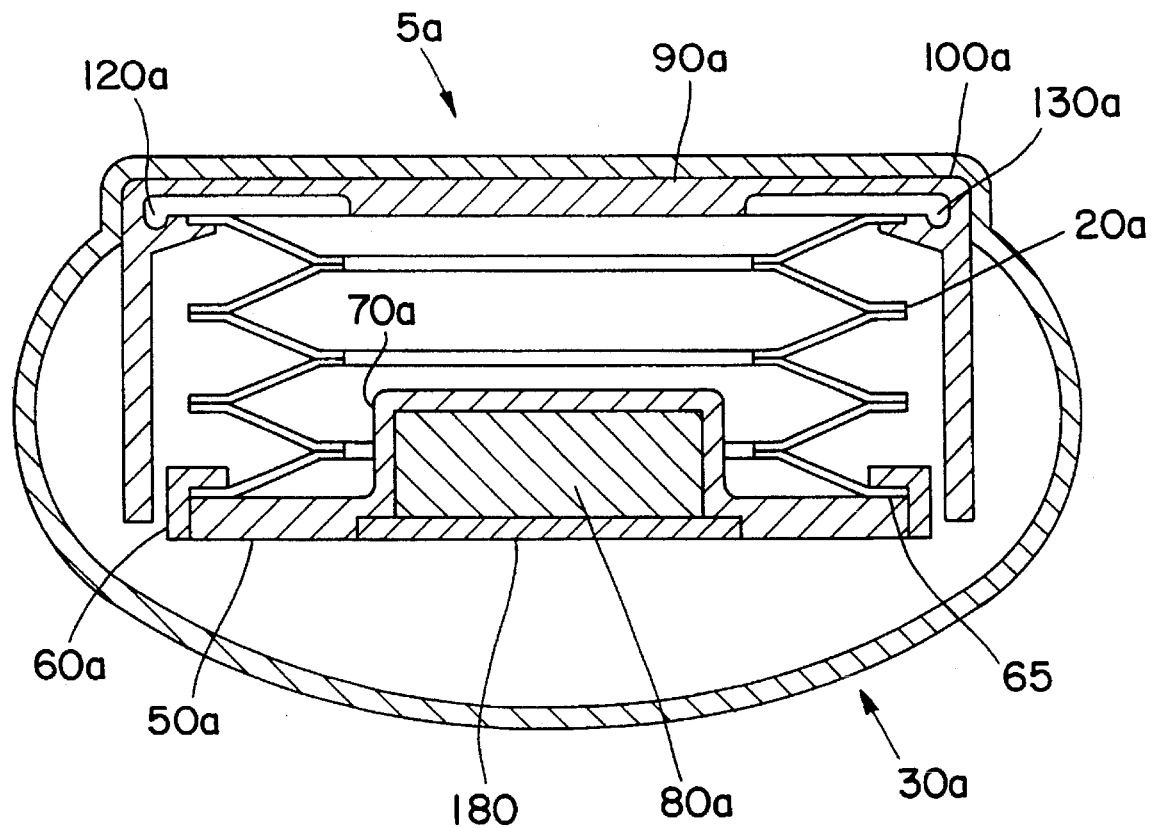
FIG. 2 is a section view of the artificial urethral sphincter.

Other and further embodiments of the present invention may be provided. Referring now to FIG. 2, another embodiment of the present invention is shown in which like parts to those in FIG. 1 are similarly numbered with the addition of the suffix "a", and in FIG. 3 a further embodiment is shown wherein like parts to those in FIGS. 1–2 are similarly numbered with the suffix "b".

FIG. 2 is a section view of artificial urethral sphincter 5a with elastomeric jacket 30a. Elastomeric bellows 20a is attached to lower reservoir cover 50a via clamp ring 60a. Clamp ring 60a is ultrasonically welded to lower reservoir cover 50a. Elastomeric bellows 20a is fitted into space 65, between lower reservoir cover 50a and clamp ring 60a.

Terminal end of elastomeric bellows 20a is attached to upper reservoir cover 90a via bellows retention joint 100a. Running in cincture fashion on the obverse side of upper reservoir cover 90a, and beveled into the obverse side of upper reservoir 90a, is fluid plenum 130a. Extending out of upper reservoir cover 90a is fluid port 120a.

Extending out from the center portion of lower reservoir cover 50a and into elastomeric bellows 20a is magnet well 70a. Inside magnet well 70a is magnet 80a. Covering magnet well 70a and magnet 80a is magnet cover 180. Magnet cover 180 is ultrasonically welded to lower reservoir cover 50a.

Figure 3:
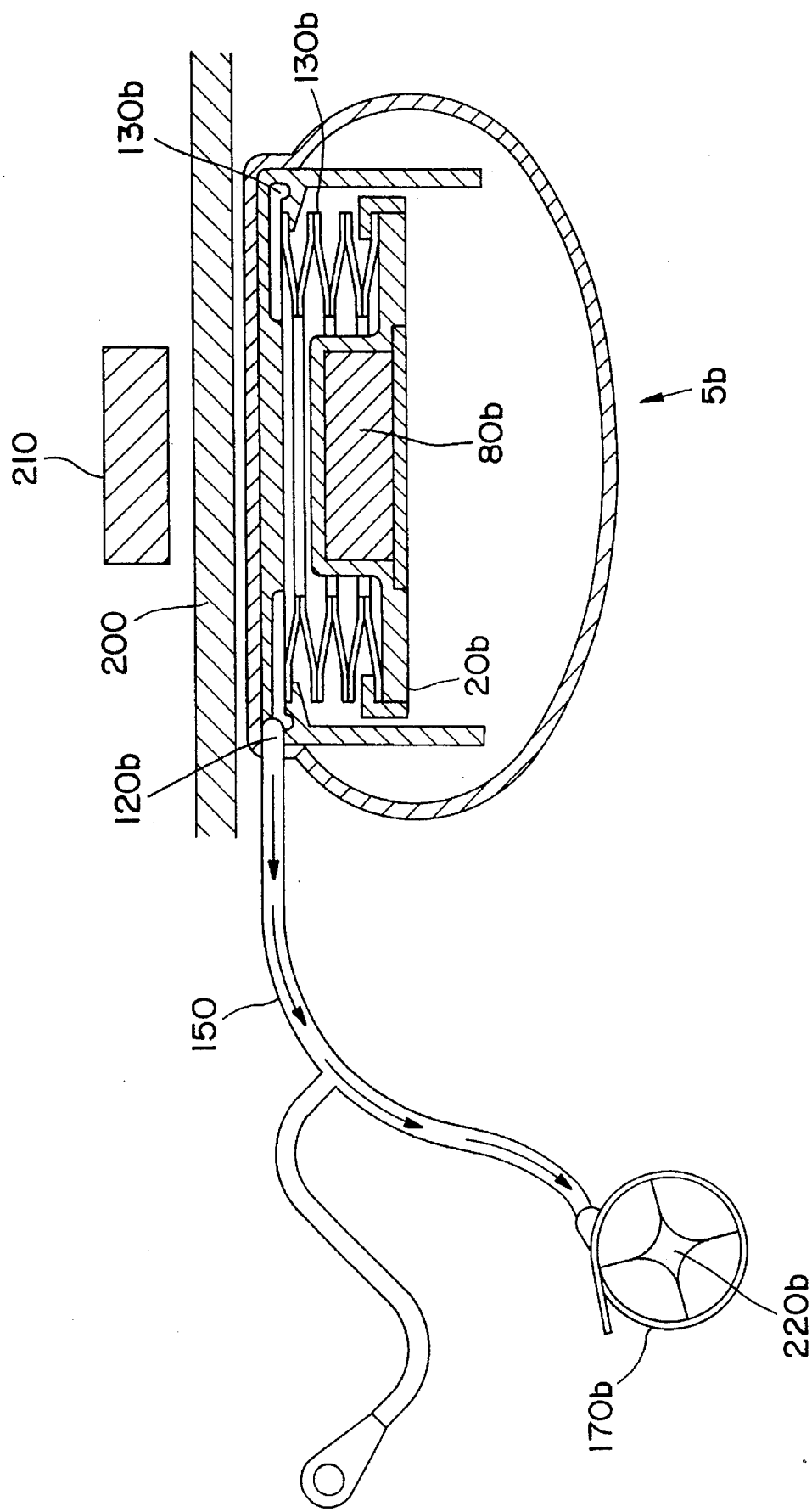
FIG. 3 is a partially sectioned assembly view of the artificial urethral sphincter in the closed position.

FIG. 3 shows a cutaway of the artificial urethral sphincter 5b implanted in a body with arrows showing the direction of fluid flow. Integument 200 is shown where the external magnet 210 would be placed to affect the closure of elastomeric bellows 20b. The attractive forces between external magnet 210 and magnet 80b allows elastomeric bellows 20b to collapse inward and toward external magnet 210. As elastomeric bellows 20b collapses inwards, fluid contained in elastomeric bellows 20b is forced through fluid channels 110b, into fluid plenum 130b.

Fluid is forced out fluid port 120b, and into fluid conduit 150b. Fluid in turn fills urethral cuff 170b inflating urethral cuff 170b and closing off the urethra 220b, thus holding back urine.

We claim:

1. An implantable urethral sphincter prosthesis, for occluding the urethra in a human being, by circumferentially surrounding and compressing the urethra, controlled through the application or removal of an external magnet on the exterior surface of the skin, over the implanted device, where the working pressure of said implanted device is adjusted percutaneously or non invasively, where said implantable prosthesis comprises:

a) an implantable assembly consisting of:
   1) an elastomeric bellows;
   2) an internal magnet located inside said elastomeric bellows;
   3) said elastomeric bellows and said internal magnet being encased in a rigid polymer housing;
   4) a fluid conduit connected to said rigid polymer housing;
   5) a fluid port, including a fluid of a predetermined fluid level and working pressure, connected to said fluid conduit;
   6) an inflatable cuff connected to said fluid conduit;

b) an external magnet means, placed on the outside exterior surface of the skin over the site of the implanted urethral sphincter prosthesis, for causing a collapse of the elastomeric bellows inside the rigid polymer housing, thereby forcing said fluid into the inflatable cuff such that the cuff inflates radially and inwardly occluding the urethra;

and said external magnet means, when removed from the exterior surface of the skin over the site of the implanted urethral sphincter device, for causing an expansion of the elastomeric bellows inside the rigid polymer housing, thereby drawing fluid from the inflatable cuff causing the inflatable cuff to deflate inwardly and radially.

2. The prosthesis of claim 1, where the fluid level and working pressure within the prosthesis are adjusted percutaneously through the application of fluid through the fluid port, or non invasively by decreasing or increasing the distance between the external magnet means and internal magnet.

3. The prosthesis of claim 1, where said elastomeric bellows is filled with an incompressible fluid.

4. The prosthesis of claim 1, where both said external magnet means and internal magnet are constructed of a high energy rare earth product.

5. The prosthesis of claim 3, wherein said incompressible fluid is a physiologic saline.

6. The prosthesis of claim 4, wherein the high energy rare earth product is a combination of neodymium, iron, and boron.

7. The prosthesis of claim 1 where said rigid polymer housing is covered by a biocompatible material with a textured surface.

8. The prosthesis of claim 1 where said fluid conduit is constructed of a biocompatible material with a textured surface.

* * * * *